(12) United States Patent
Kanauchi et al.

(10) Patent No.: US 10,815,172 B2
(45) Date of Patent: Oct. 27, 2020

(54) 1,3-BUTADIENE SEPARATION AND RECOVERY METHOD AND 1,3-BUTADIENE SEPARATION AND RECOVERY APPARATUS

(71) Applicant: ZEON CORPORATION, Chiyoda-ku, Tokyo (JP)

(72) Inventors: Masanobu Kanauchi, Chiba (JP); Seiji Futamura, Fujisawa (JP); Kenichi Otsubo, Yachiyo (JP)

(73) Assignee: ZEON CORPORATION, Chiyoda-ku, Tokyo (JP)

(*) Notice: Subject to any disclaimer, the term of this patent is extended or adjusted under 35 U.S.C. 154(b) by 0 days.

(21) Appl. No.: 16/479,337

(22) PCT Filed: Jan. 25, 2018

(86) PCT No.: PCT/JP2018/002239
§ 371 (c)(1),
(2) Date: Jul. 19, 2019

(87) PCT Pub. No.: WO2018/143042
PCT Pub. Date: Aug. 9, 2018

(65) Prior Publication Data
US 2019/0337871 A1     Nov. 7, 2019

(30) Foreign Application Priority Data

Feb. 1, 2017 (JP) ................................ 2017-017007

(51) Int. Cl.
*C07C 11/167* (2006.01)
*B01D 3/14* (2006.01)
(Continued)

(52) U.S. Cl.
CPC ............ *C07C 11/167* (2013.01); *B01D 3/141* (2013.01); *B01D 3/40* (2013.01); *C07C 7/04* (2013.01)

(58) Field of Classification Search
CPC ......... C07C 6/04; C07C 11/10; C07C 11/107; C07C 11/08; B01D 3/141; B01D 3/40;
(Continued)

(56) References Cited

U.S. PATENT DOCUMENTS 7,226,527 B2 * 6/2007 Bohner ................. B01D 3/141
                                                         203/2
2008/0188696 A1    8/2008 Stephan et al.
(Continued)

FOREIGN PATENT DOCUMENTS

EP         1083160 A1      3/2001
JP         S45017407 B1    6/1970
(Continued)

OTHER PUBLICATIONS

Aug. 6, 2019, International Preliminary Report on Patentability issued in the International Patent Application No. PCT/JP2018/002239.

(Continued)

*Primary Examiner* — Sharon Pregler
(74) *Attorney, Agent, or Firm* — Kenja IP Law PC

(57) ABSTRACT

Disclosed is a 1,3-butadiene separation and recovery method which can reduce the amount of 1,3-butadiene polymer produced when 1,3-butadiene is separated and recovered from a mixed fluid containing 1,3-butadiene. The method includes an extractive distillation step of performing extractive distillation of the mixed fluid to obtain a fraction containing crude 1,3-butadiene, and a dividing wall distillation step of performing dividing wall distillation of the fraction containing crude 1,3-butadiene to obtain a fraction containing an impurity having a higher boiling point than 1,3-butadiene, a fraction containing an impurity having a lower boiling point than 1,3-butadiene, and a fraction containing high-purity 1,3-butadiene.

8 Claims, 2 Drawing Sheets

(51) Int. Cl.
  *B01D 3/40* (2006.01)
  *C07C 7/04* (2006.01)
(58) Field of Classification Search
  CPC . B01D 3/14; B01D 3/148; B01D 3/42; B01D 5/006
  See application file for complete search history.

(56) References Cited

U.S. PATENT DOCUMENTS

2015/0191403 A1* 7/2015 Nakahara .................. C07C 7/10
 585/810
2016/0074770 A1 3/2016 Schreieder et al.
2018/0370875 A1* 12/2018 Manchekar ............... C07C 7/08

FOREIGN PATENT DOCUMENTS

| JP | 2002053871 A | 2/2002 |
| JP | 2008515953 A | 5/2008 |
| JP | 2016524522 A | 8/2016 |
| WO | 9951552 A1 | 10/1999 |

OTHER PUBLICATIONS

Apr. 10, 2018, International Search Report issued in the International Patent Application No. PCT/JP2018/002239.

* cited by examiner

US 10,815,172 B2

1,3-BUTADIENE SEPARATION AND RECOVERY METHOD AND 1,3-BUTADIENE SEPARATION AND RECOVERY APPARATUS

TECHNICAL FIELD

The present disclosure relates to a 1,3-butadiene separation and recovery method and a 1,3-butadiene separation and recovery apparatus, and in particular, relates to a 1,3-butadiene separation and recovery method and a 1,3-butadiene separation and recovery apparatus that can reduce the amount of 1,3-butadiene polymer that is produced during separation and recovery of 1,3-butadiene from a mixed fluid containing 1,3-butadiene.

BACKGROUND

Methods using extractive distillation are known as methods for separation and recovery of high-purity 1,3-butadiene from a mixed fluid such as a C4 fraction obtained during the production of ethylene through cracking of naphtha.

One specific example of a method for separation and recovery of 1,3-butadiene from a mixed fluid such as a C4 fraction using extractive distillation is a method for separation and recovery of high-purity 1,3-butadiene which includes first extractive distillation wherein butanes and butenes that are less soluble in solvent than butadienes (1,2-butadiene and 1,3-butadiene) are distilled for separation; second extractive distillation wherein acetylenes that are more solubility in solvent than butadiene are drained while distilling a fraction containing a high concentration of butadiene; and purifying the fraction obtained in the second extractive distillation (for example, refer to Patent Literature (PTL) 1).

The 1,3-butadiene separation and recovery method using extractive distillation can separate and remove methylacetylene (impurity having a lower boiling point than 1,3-butadiene) and ethylacetylene (impurity having a higher boiling point than 1,3-butadiene) that can act as a hindrance in a polymerization reaction for preparing butadiene synthetic rubber or the like.

CITATION LIST

Patent Literature

PTL 1: JPS45-17407B

SUMMARY

Technical Problem

However, in the 1,3-butadiene separation and recovery method using extractive distillation described above, it has not been possible to inhibit the production of 1,3-butadiene polymer, which may act as a cause of apparatus staining.

Accordingly, an objective of the present disclosure is to provide a 1,3-butadiene separation and recovery method that can reduce the amount of 1,3-butadiene polymer that is produced during separation and recovery of 1,3-butadiene from a mixed fluid containing 1,3-butadiene, and a 1,3-butadiene separation and recovery apparatus.

Solution to Problem

The present disclosure aims to advantageously solve the problem set forth above by disclosing a 1,3-butadiene separation and recovery method for separating and recovering 1,3-butadiene from a mixed fluid containing 1,3-butadiene, the method comprising: an extractive distillation step of performing extractive distillation of the mixed fluid to obtain a fraction containing crude 1,3-butadiene; and a dividing wall distillation step of performing dividing wall distillation of the fraction containing crude 1,3-butadiene to obtain a fraction containing an impurity having a higher boiling point than 1,3-butadiene, a fraction containing an impurity having a lower boiling point than 1,3-butadiene, and a fraction containing high-purity 1,3-butadiene. Performing dividing wall distillation of the fraction containing crude 1,3-butadiene in this manner can reduce heat load and can reduce the amount of 1,3-butadiene polymer that is produced during separation and recovery of 1,3-butadiene from the mixed fluid containing 1,3-butadiene. Accordingly, it is possible to reduce the frequency of polymer cleaning which needs to be performed while the operation of a 1,3-butadiene separation and recovery apparatus is suspended.

The term "crude 1,3-butadiene" as used herein means "a mixed fluid containing 1,3-butadiene, from which impurities such as butanes and butenes have been separated and removed by extractive distillation." The term "high-purity 1,3-butadiene" as used herein refers to "1,3-butadiene of higher concentration than 1,3-butadiene concentration in crude 1,3-butadiene". The "1,3-butadiene concentration" can be measured by gas chromatography.

The term "dividing wall distillation" as used herein refers to the separation of a material that is to be distilled into three or more (preferably three) fractions through a single distillation operation. This dividing wall distillation can be implemented, for example, using a vertical dividing wall column or the like.

In the 1,3-butadiene separation and recovery method of the present disclosure, the extractant in the extractive distillation step is preferably an amide compound, and more preferably dimethylformamide. The use of an amide compound as an extractant, and particularly of dimethylformamide, enables efficient implementation of extractive distillation.

In the 1,3-butadiene separation and recovery method of the present disclosure, the dividing wall distillation in the dividing wall distillation step is preferably performed in the presence of not less than 1 mass ppm and not more than 100 mass ppm of a polymerization inhibitor relative to the crude 1,3-butadiene. By performing the dividing wall distillation in the presence of the amount of a polymerization inhibitor set forth above, the occurrence of a polymerization reaction during the dividing wall distillation can be inhibited, and the occurrence of staining or blocking in a dividing wall column in which the dividing wall distillation is carried out can be prevented.

In the 1,3-butadiene separation and recovery method of the present disclosure, it is preferred that the dividing wall distillation in the dividing wall distillation step is performed in a dividing wall distillation column and a polymerization inhibitor is fed from an vertical direction upper part of the dividing wall column. By feeding the polymerization inhibitor from the vertical direction upper part of the dividing wall column, the polymerization inhibitor can be distributed throughout the entire dividing wall column.

The term "vertical direction upper part of a dividing wall column" as used herein refers to "an upper part corresponding to not less than 70% and not more than 100% of the vertical direction height of the dividing wall column".

In the 1,3-butadiene separation and recovery method of the present disclosure, the fraction containing high-purity 1,3-butadiene is preferably a gas. When the fraction containing high-purity 1,3-butadiene is a gas, this can prevent inclusion of the polymerization inhibitor in the high-purity 1,3-butadiene. As a consequence, the high-purity 1,3-butadiene can advantageously be used in the preparation of a polymer such as polybutadiene.

The 1,3-butadiene separation and recovery method of the present disclosure preferably further includes a removal step of removing the polymerization inhibitor from the fraction containing high-purity 1,3-butadiene. When the polymerization inhibitor is removed from the fraction containing high-purity 1,3-butadiene, inclusion of the polymerization inhibitor in the separated and recovered 1,3-butadiene can be prevented. As a consequence, the high-purity 1,3-butadiene can be advantageously used in the preparation of a polymer such as polybutadiene.

The present disclosure aims to advantageously solve the problem set forth above by disclosing a 1,3-butadiene separation and recovery apparatus comprising: an extractive distillation section that includes a feeding port for feeding of a mixed fluid containing 1,3-butadiene and that performs extractive distillation of the mixed fluid to obtain a fraction containing crude 1,3-butadiene; and a dividing wall distillation section that includes a feeding port for feeding of the fraction containing crude 1,3-butadiene and that performs dividing wall distillation of the fraction containing crude 1,3-butadiene to obtain a fraction containing an impurity having a higher boiling point than 1,3-butadiene, a fraction containing an impurity having a lower boiling point than 1,3-butadiene, and a fraction containing high-purity 1,3-butadiene. Performing dividing wall distillation of the fraction containing crude 1,3-butadiene can reduce heat load and can reduce the amount of 1,3-butadiene polymer that is produced during separation and recovery of 1,3-butadiene from the mixed fluid containing 1,3-butadiene. As a consequence, it is possible to reduce the frequency of polymer cleaning which needs to be performed while the operation of the 1,3-butadiene separation and recovery apparatus is suspended.

Advantageous Effect

According to the present disclosure, it is possible to reduce the amount of a 1,3-butadiene polymer that is produced during separation and recovery of 1,3-butadiene from a mixed fluid containing 1,3-butadiene.

DETAILED DESCRIPTION

Figure 1:
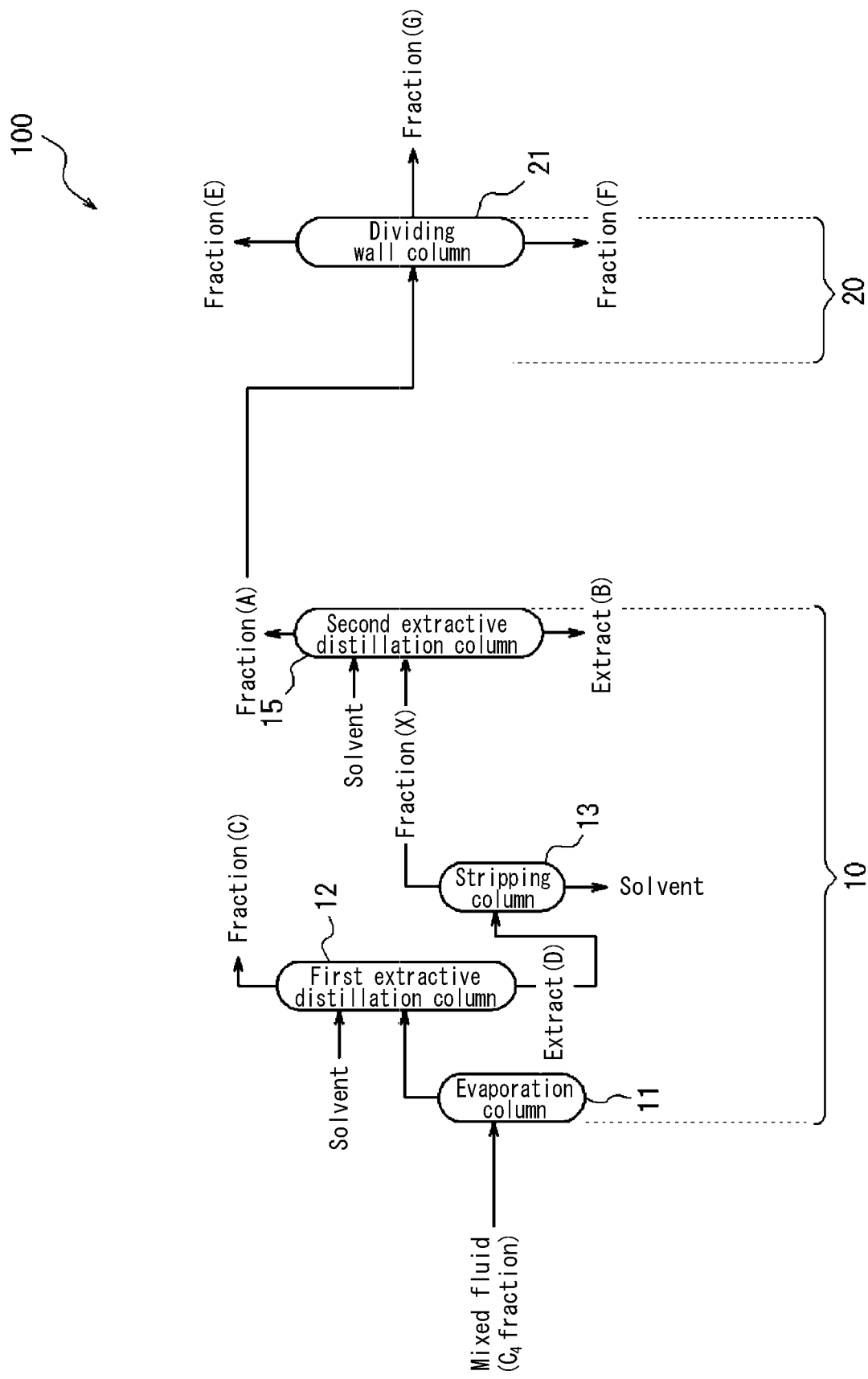
FIG. 1 schematically illustrates configuration of one example of a 1,3-butadiene separation and recovery apparatus for carrying out a 1,3-butadiene separation and recovery method according to the present disclosure.

The following provides a detailed description of embodiments of the present disclosure.

The 1,3-butadiene separation and recovery method of the present disclosure can be used in separation and recovery of 1,3-butadiene from a 1,3-butadiene-containing mixed fluid feedstock, such as a C4 fraction. The 1,3-butadiene separation and recovery apparatus of the present disclosure can be suitably used, for example, in separation and recovery of 1,3-butadiene by the 1,3-butadiene separation and recovery method of the present disclosure.

(1,3-Butadiene Separation and Recovery Method)

The 1,3-butadiene separation and recovery method of the present disclosure is a method for separating and recovering 1,3-butadiene from a mixed fluid containing 1,3-butadiene. The 1,3-butadiene separation and recovery method of the present disclosure comprises: a step of performing estractive distillation of the mixed fluid containing 1,3-butadiene to obtain a fraction containing crude 1,3-butadiene (extractive distillation step); and a step of performing dividing wall distillation of the fraction containing crude 1,3-butadiene, optionally in the presence of a polymerization inhibitor, to obtain a fraction containing impurities having a higher boiling point than 1,3-butadiene, a fraction containing impurities having a lower boiling point than 1,3-butadiene, and a fraction containing high-purity 1,3-butadiene (dividing wall distillation step), and may optionally, furthermore comprises a step of removing the polymerization inhibitor used in the dividing wall distillation from the fraction containing high-purity 1,3-butadiene (removal step).

By performing dividing wall distillation of the fraction containing crude 1,3-butadiene in the 1,3-butadiene separation and recovery method of the present disclosure, heat load can be reduced and the amount of the 1,3-butadiene polymer produced during separation and recovery of 1,3-butadiene from the mixed fluid containing 1,3-butadiene can be reduced. As a consequence, it is possible to perform recovery and separation of 1,3-butadiene at a high yield.

By performing dividing wall distillation in the presence of a polymerization inhibitor in the dividing wall distillation step of the 1,3-butadiene separation and recovery method of the present disclosure, it is possible to inhibit the occurrence of a polymerization reaction during dividing wall distillation. In general, a polymerization reaction tends to readily occur during dividing wall distillation because dividing wall distillation is implemented with a comparatively high operating pressure and temperature compared to normal distillation. However, by performing the dividing wall distillation in the presence of a polymerization inhibitor, the occurrence of a polymerization reaction during dividing wall distillation can be inhibited, and the occurrence of staining or blocking of an apparatus used to perform the dividing wall distillation (for example, a dividing wall column) can be prevented.

By removing the polymerization inhibitor used in dividing wall distillation from the fraction containing high-purity 1,3-butadiene, inclusion of the polymerization inhibitor in the high-purity 1,3-butadiene can be prevented. More specifically, when the polymerization of high-purity 1,3-butadiene is to be carried out, the polymerization is inhibited if the polymerization inhibitor is contained in the high-purity 1,3-butadiene. However, by removing the polymerization inhibitor used in dividing wall distillation, it is possible to prevent the polymerization from being inhibited when polymerization of high-purity 1,3-butadiene is to be carried out.

By withdrawing the fraction containing high-purity 1,3-butadiene as a gas in the dividing wall distillation step of the 1,3-butadiene separation and recovery method of the present disclosure, inclusion of the polymerization inhibitor in the high-purity 1,3-butadiene can be prevented. More specifically, when polymerization of high-purity 1,3-butadiene is to be carried out, polymerization is inhibited if a polymerization inhibitor is contained in the high-purity 1,3-butadiene. However, by withdrawing the fraction containing high-purity 1,3-butadiene from the dividing wall column as a gas, it is possible to prevent the inclusion of the polymerization inhibitor in the high-purity 1,3-butadiene to thereby prevent the inhibition of polymerization when polymerization of the high-purity 1,3-butadiene is to be carried out.

<Mixed Fluid Containing 1,3-Butadiene>

The mixed fluid containing 1,3-butadiene which is used in the separation and recovery of 1,3-butadiene is not specifically limited, as long as it comprises 1,3-butadiene, and may be any C4 hydrocarbon mixture comprising 1,3-butadiene, butane, butene, vinylacetylene, methylacetylene, ethylacetylene, and the like, such as the C4 fraction obtained in the production of ethylene through cracking of naphtha.

The mixed fluid preferably contains 5 mass % or more of 1,3-butadiene. When the content of 1,3-butadiene in the mixed fluid is 5 mass % or more, 1,3-butadiene can be efficiently separated and recovered from the mixed fluid.

Note that, normally, the content of 1,3-butadiene in the mixed fluid is 30 mass % to 50 mass %.

<Extractive Distillation Step>

In the extractive distillation step of the 1,3-butadiene separation and recovery method of the present disclosure, extractive distillation of a mixed fluid containing 1,3-butadiene is performed to separate, from the mixed fluid, impurities of different solubility in the extractant used in the extractive distillation than 1,3-butadiene, to obtain a fraction containing crude 1,3-butadiene.

[Extractive Distillation]

Extractive distillation may be constituted by a single-stage extractive distillation or may be constituted by a two or more stage extractive distillation.

With reference to the drawings, the following describes a case in which extractive distillation is performed in two stages (first extractive distillation and second extractive distillation), i.e., a case in which extractive distillation is performed in an extractive distillation section that includes a first extractive distillation column that performs first extractive distillation and a second extractive distillation column that performs second extractive distillation.

FIG. 1 is a schematic configuration of an example of a 1,3-butadiene separation and recovery apparatus for carrying out a 1,3-butadiene separation and recovery method according to the present disclosure.

In FIG. 1, an extractive distillation section 10 includes, for example, an evaporation column 11 that vaporizes a mixed fluid containing 1,3-butadiene such as a C4 fraction; a first extractive distillation column 12 that performs extractive distillation (first extractive distillation) of the mixed fluid vaporized in the evaporation column 11 to separate the mixed fluid into a fraction (C) and an extract (D); a stripping column 13 that removes the solvent from the extract (D); and a second extractive distillation column 15 that performs extractive distillation (second extractive distillation) of a fraction (X), obtained by removing the solvent from the extract (D), to separate the fraction (X) into a fraction (A) (fraction containing crude 1,3-butadiene) and an extract (B).

In the first extractive distillation column 12, a solvent is fed from a higher level (vertical direction upper side) relative to a feeding level of the mixed fluid vaporized in the evaporation column 11, and extractive distillation (first extractive distillation) of the mixed fluid is performed so as to distill the fraction (C) containing butanes and butenes that are less soluble in the solvent than 1,3-butadiene from the top of the column and drain the extract (D) containing 1,3-butadiene, vinylacetylene, methylacetylene, ethylacetylene, and the like from the bottom of the column.

The solvent that is fed into the first extractive distillation column 12 may be a known solvent that is used in extractive distillation of a C4 fraction, such as any of the solvents described in WO 99/051552 A1, for example. Of these solvents, an amide compound is preferable, and dimethylformamide is more preferable. The use of an amide compound as an extractant, and particularly of dimethylformamide, enables efficient implementation of extractive distillation.

In the stripping column 13, the solvent is drained from the bottom of the column and a fraction (X) containing 1,3-butadiene, vinylacetylene, methylacetylene, ethylacetylene, and the like is distilled from the top of the column. Note that solvent recovered by the stripping column 13 may optionally be reused in the first extractive distillation column 12, the subsequently described second extractive distillation column 15, or the like.

In the second extractive distillation column 15, a solvent is fed from a higher level (vertical direction upper side) relative to a feeding level of the fraction (X) containing 1,3-butadiene and vinylacetylene that has been distilled from the stripping column 13, and extractive distillation (second extractive distillation) of the fraction containing 1,3-butadiene, vinylacetylene, methylacetylene, ethylacetylene and the like is performed to distill a fraction (A) containing crude 1,3-butadiene from the top of the column and drain an extract (B) containing vinylacetylene and the like that are more soluble in the solvent than 1,3-butadiene from the bottom of the column.

The solvent that is fed into the second extractive distillation column 15 may be a known solvent that is used in extractive distillation of a C4 fraction, such as any of the solvents described in WO 99/051552 A1, for example. Of these solvents, an amide compound is preferable, and dimethylformamide is more preferable. The use of an amide compound as an extractant, and particularly of dimethylformamide, enables efficient implementation of extractive distillation.

<Dividing Wall Distillation Step>

In the dividing wall distillation step of the 1,3-butadiene separation and recovery method of the present disclosure, dividing wall distillation of the fraction containing crude 1,3-butadiene is performed to separate impurities having a higher boiling point than 1,3-butadiene and impurities having a lower boiling point than 1,3-butadiene from the fraction containing crude 1,3-butadiene to thereby obtain a fraction containing high-purity 1,3-butadiene. Performing dividing wall distillation of the fraction containing crude 1,3-butadiene in this manner can reduce heat load and can reduce, the amount of 1,3-butadiene polymer that is produced during separation and recovery of 1,3-butadiene from the mixed fluid containing 1,3-butadiene, compared to a situation in which removal of high boiling point components by distillation and removal of low boiling point components by distillation are implemented separately in two stages. As a consequence, it is possible to reduce the frequency of polymer cleaning which needs to be performed while the operation of a 1,3-butadiene separation and recovery apparatus is suspended.

[Dividing Wall Distillation]

Dividing wall distillation can provide a fraction containing an impurity having a higher boiling point than 1,3-butadiene, a fraction containing an impurity having a lower boiling point than 1,3-butadiene, and a fraction containing high-purity 1,3-butadiene, by using a dividing wall column to discharge high boiling point components from the bottom of the column, discharge middle boiling point components from a central region of the column, and discharge low boiling point components from the top of the column, as described in JP 2016-524522 A, for example.

—Dividing Wall Column—

The dividing wall column may, for example, be a vertical dividing wall column in which a dividing wall is disposed in a longitudinal direction of the column such as described in JP 2016-524522 A, for example. The dividing wall divides the inside of the column into, for example, a feeding section (left side of dividing wall), a removal section (right side of dividing wall), an upper joined column section (rectifying section), and a lower joined column section (stripping section).

A feeding port (feeding inlet) for feeding of the fraction containing crude 1,3-butadiene that is to be subjected to dividing wall distillation is normally disposed in a central region of the feeding section (i.e., between an upper region and a lower region of the feeding section). One or more further feeding ports (feeding inlets) may be disposed in the central region of the feeding section.

In general, one or more side-stream withdrawing sections are disposed in a central region of the removal section (i.e., between an upper region and a lower region of the removal section). One or more further side-stream outlets may be disposed in the central region of the removal section.

Compared to a conventional case in which a high boiling distillation column and a low boiling distillation column are directly connected (for example, a case illustrated in FIG. 2 described further below), the use of a dividing wall column such as described above can provide roughly 30% cost reduction and allow reduction of the residence time of the processing target substance, and enables dividing wall distillation of a mixed fluid (separation and removal of high boiling point components and low boiling point components from the mixed fluid) with low heat load.

With reference to the drawings, the following describes a case in which dividing wall distillation is performed using a dividing wall distillation section composed of a dividing wall column.

In FIG. 1, a dividing wall distillation section 20 includes, for example, a dividing wall column 21 that performs dividing wall distillation of the fraction (A) containing crude 1,3-butadiene that has been distilled from the top of the column of the second extractive distillation column 15.

The dividing wall column 21, for example, distills a fraction (E) containing low boiling point impurities such as methylacetylene (boiling point: −23.2° C.) contained in the fraction (A) obtained in the second extractive distillation column 15 from the top of the column, drains a fraction (F) containing high boiling point impurities such as ethylacetylene (boiling point: 8.08° C.) and 1,2-butadiene (boiling point: 18° C.) from the bottom of the column, and distills high-purity 1,3-butadiene from a central region of the column as a fraction (G) which is enriched with 1,3-butadiene (boiling point: −4.4° C.).

In general, a polymerization reaction tends to readily occur during dividing wall distillation because dividing wall distillation is implemented with a comparatively high operating pressure and temperature compared to normal distillation. Although a polymerization reaction readily occurs inside the dividing wall column 21, the occurrence of a polymerization reaction during dividing wall distillation can be inhibited and the occurrence of staining or blocking of the dividing wall column 21 can be prevented by performing the dividing wall distillation in the presence of a polymerization inhibitor.

—Polymerization Inhibitor—

Specific examples of polymerization inhibitors that may be used include, but are not specifically limited to, 4-tert-butylcatechol (TBC) and diethylhydroxylamine (DEHA).

Although no specific limitations are placed on the amount of the polymerization inhibitor that is present during dividing wall distillation, the amount is preferably 1 mass ppm or more relative to crude 1,3-butadiene from a viewpoint of inhibiting a polymerization reaction during dividing wall distillation and is preferably 100 mass ppm or less relative to crude 1,3-butadiene from a viewpoint of reducing the polymerization inhibitor content in high-purity 1,3-butadiene.

The location at which the polymerization inhibitor is fed is not specifically limited so long as the polymerization inhibitor is present during dividing wall distillation. For example, the polymerization inhibitor may be fed directly into the dividing wall column 21 or may be fed into a pipe directly preceding the dividing wall column 21. The polymerization inhibitor can be distributed throughout the entire dividing wall column 21 by feeding the polymerization inhibitor at a vertical direction upper part that is at a higher level (vertical direction upper side) relative to a feeding level of the fraction (A) containing crude 1,3-butadiene in the dividing wall column 21.

Also note that by withdrawing the fraction containing high-purity 1,3-butadiene from the dividing wall column 21 as a gas in the dividing wall distillation section 20, inclusion of polymerization inhibitor in the high-purity 1,3-butadiene can be prevented. More specifically, when polymerization of high-purity 1,3-butadiene is to be carried out, polymerization is inhibited if a polymerization inhibitor is contained in the high-purity 1,3-butadiene. However, by withdrawing the fraction containing high-purity 1,3-butadiene from the dividing wall column 21 as a gas, it is possible to prevent the inclusion of the polymerization inhibitor in the high-purity 1,3-butadiene to thereby prevent the inhibition of polymerization when polymerization of the high-purity 1,3-butadiene is to be carried out.

<Removal Step>

In the 1,3-butadiene separation and recovery method of the present disclosure, it is preferred that the polymerization inhibitor used in the dividing wall distillation in the dividing wall column 21 is removed from the fraction containing high-purity 1,3-butadiene. By removing the polymerization inhibitor used in dividing wall distillation in the dividing wall column 21 from the fraction containing high-purity 1,3-butadiene in this manner, inclusion of the polymerization inhibitor in the high-purity 1,3-butadiene can be prevented. More specifically, when polymerization of high-purity 1,3-butadiene is to be carried out, polymerization is inhibited if a polymerization inhibitor is contained in the high-purity 1,3-butadiene. However, by removing the polymerization inhibitor used in dividing wall distillation in the dividing wall column 21 from the fraction containing high-purity 1,3-butadiene, it is possible to prevent the polymerization from being inhibited when polymerization of the high-purity 1,3-butadiene is to be carried out.

Examples of methods by which the polymerization inhibitor is removed include, but are not specifically limited to, a method in which the fraction containing high-purity 1,3-butadiene is washed with water and a method in which the polymerization inhibitor is separated by distillation.

(1,3-Butadiene Separation and Recovery Apparatus)

The 1,3-butadiene separation and recovery apparatus of the present disclosure can suitably be used in separation and recovery of 1,3-butadiene by the 1,3-butadiene separation and recovery method set forth above. One example of the 1,3-butadiene separation and recovery apparatus of the present disclosure has, for example, a configuration such as that illustrated in FIG. 1.

A separation and recovery apparatus 100 illustrated in FIG. 1 includes an extractive distillation section 10 that performs extractive distillation of a mixed fluid used as a feedstock to obtain a fraction (A) containing crude 1,3-butadiene, and a dividing wall distillation section 20 that performs dividing wall distillation of the fraction (A) obtained in the extractive distillation section 10 to obtain a fraction (E) containing impurities having a lower boiling point than 1,3-butadiene, a fraction (F) containing impurities having a higher boiling point than 1,3-butadiene, and high-purity 1,3-butadiene as a fraction (G) enriched with 1,3-butadiene. The mixed fluid used in the separation and recovery apparatus 100 may, for example, be a C4 fraction that is produced in the production of ethylene through cracking of naphtha.

<Extractive Distillation Section>

In FIG. 1, the extractive distillation section 10 includes, for example, an evaporation column 11 that vaporizes a mixed fluid containing 1,3-butadiene, such as a C4 fraction; a first extractive distillation column 12 that includes a feeding port for feeding of a mixed fluid containing 1,3-butadiene and that performs extractive distillation (first extractive distillation) of the mixed fluid vaporized in the evaporation column 11 fed via the feeding port to separate the mixed fluid into a fraction (C) and an extract (D); a stripping column 13 that removes the solvent from the extract (D); and a second extractive distillation column 15 that includes a feeding port for feeding of a fraction (X) obtained by removing the solvent from the extract (D) and that performs extractive distillation (second extractive distillation) of the fraction (X) fed via the feeding port to separate the fraction (X) into a fraction (A) (fraction containing crude 1,3-butadiene) and an extract (B).

In the first extractive distillation column 12, a solvent is fed from a higher level (vertical direction upper side) relative to a feeding level of the mixed fluid vaporized in the evaporation column 11 and extractive distillation (first extractive distillation) of the mixed fluid is performed to distill a fraction (C) containing butanes and butenes that are less soluble in the solvent than 1,3-butadiene from the top of the column and drain an extract (D) containing 1,3-butadiene and vinylacetylene from the bottom of the column.

The solvent that is fed into the first extractive distillation column 12 may be a known solvent that is used in extractive distillation of a C4 fraction, such as any of the solvents described in WO 99/051552 A1, for example. Of these solvents, an amide compound is preferable, and dimethylformamide is more preferable. The use of an amide compound as an extractant, and particularly of dimethylformamide, enables efficient implementation of extractive distillation.

In the stripping column 13, the solvent is drained from the bottom of the column, and the fraction (X) containing 1,3-butadiene, vinylacetylene, methylacetylene, ethylacetylene and the like is distilled from the top of the column. Note that the solvent recovered by the stripping column 13 may be optionally reused in the first extractive distillation column 12, the second extractive distillation column 15 or the like.

In the second extractive distillation column 15, a solvent is fed from a higher level (vertical direction upper side) relative to a feeding level of the fraction (X) containing 1,3-butadiene and vinylacetylene that has been distilled from the stripping column 13 and extractive distillation (second extractive distillation) of the fraction containing 1,3-butadiene, vinylacetylene, methylacetylene, ethylacetylene and the like is performed to distill the fraction (A) containing crude 1,3-butadiene from the top of the column and drain the extract (B) containing vinylacetylene and the like that are more soluble in the solvent than 1,3-butadiene from the bottom of the column.

The solvent that is fed into the second extractive distillation column 15 may be a known solvent that is used in extractive distillation of a C4 fraction, such as any of the solvents described in WO 99/051552 A1, for example. Of these solvents, an amide compound is preferable, and dimethylformamide is more preferable. The use of an amide compound as an extractant, and particularly of dimethylformamide, enables efficient implementation of extractive distillation.

<Dividing Wall Distillation Section>

In FIG. 1, the dividing wall distillation section 20 includes, for example, a dividing wall column 21 that includes a feeding port for feeding of the fraction (A) containing crude 1,3-butadiene and that performs dividing wall distillation of the fraction (A) containing crude 1,3-butadiene that has been distilled from the top of the column of the second extractive distillation column 15.

The dividing wall column 21, for example, distills the fraction (E) containing low boiling point impurities such as methylacetylene from the top of the column, drains the fraction (F) containing high boiling point impurities such as ethylacetylene from the bottom of the column, and distills the fraction (G) (fraction (G) containing high-purity 1,3-butadiene) enriched with 1,3-butadiene from the region of the center of the column.

Although the 1,3-butadiene separation and recovery apparatus of the present disclosure has been described above using an example, the 1,3-butadiene separation and recovery apparatus of the present disclosure is not limited to the example described above. Moreover, the configurations of the extractive distillation section 10 and the dividing wall distillation section 20 are not specifically limited to the configurations described above, and may be changed to any configurations that enable separation and recovery of 1,3-butadiene.

EXAMPLES

The following provides a more detailed description of the present disclosure through examples. However, the present disclosure is not limited to these examples.

Example 1

Separation and recovery of 1,3-butadiene was performed using the separation and recovery apparatus 100 illustrated in FIG. 1. Specifically, 1,3-butadiene was separated and recovered from a mixed fluid formed from a C4 fraction obtained in the production of ethylene through cracking of naphtha. The amount of 1,3-butadiene in the mixed fluid formed from the C4 fraction was 40 mass %.

The compositions of the fraction (A), the fraction (C), the fraction (E), the fraction (F) and the fraction (G) were measured using a gas chromatograph (7890A manufactured by Agilent Technologies) under the following conditions. The results are shown in Table 1.

Gas chromatograph: Agilent® (Agilent is a registered trademark in Japan, other countries, or both) 7890A (produced by Agilent Technologies, Inc.)
Column: Agilent 19091P-S33, 30.0 m×250 µm×5.00 µm
Column temperature: 35° C.×2.5 mins⇒heating at 5° C./min⇒100° C.⇒heating at 10° C./min⇒180° C.×10 mins
Injection temperature: 200° C.
Detector temperature: 200° C.
Carrier gas: Helium
Split ratio: 200/1
Detector: FID

TABLE 1

|  | Fraction (A) | Fraction (C) | Fraction (E) | Fraction (F) | Fraction (G) |
|---|---|---|---|---|---|
| n-butane, i-butane [mass %] | — | 14.0 | — | — | — |
| trans-2-butene [mass %] | 0.1 | 10.0 | — | — | 0.10 |
| 1-butene, iso-butene [mass %] | — | 70.0 | — | — | — |
| cis-2-butene [mass %] | 2.5 | 6.0 | — | 82.0 | 0.20 |
| 1,2-butadiene [mass %] | 0.1 | — | — | 5.0 | — |
| 1,3-butadiene [mass %] | 97.0 | — | 70.0 | 5.0 | 99.70 |
| Methyl acetylene [mass %] | 0.1 | — | 30.0 | — | — |
| Vinyl acetylene [mass %] | — | — | — | — | — |
| Ethyl acetylene [mass %] | 0.1 | — | — | 3.0 | — |
| Other [mass %] | 0.1 | — | — | 5.00 | — |

Comparative Example 1

Figure 2:
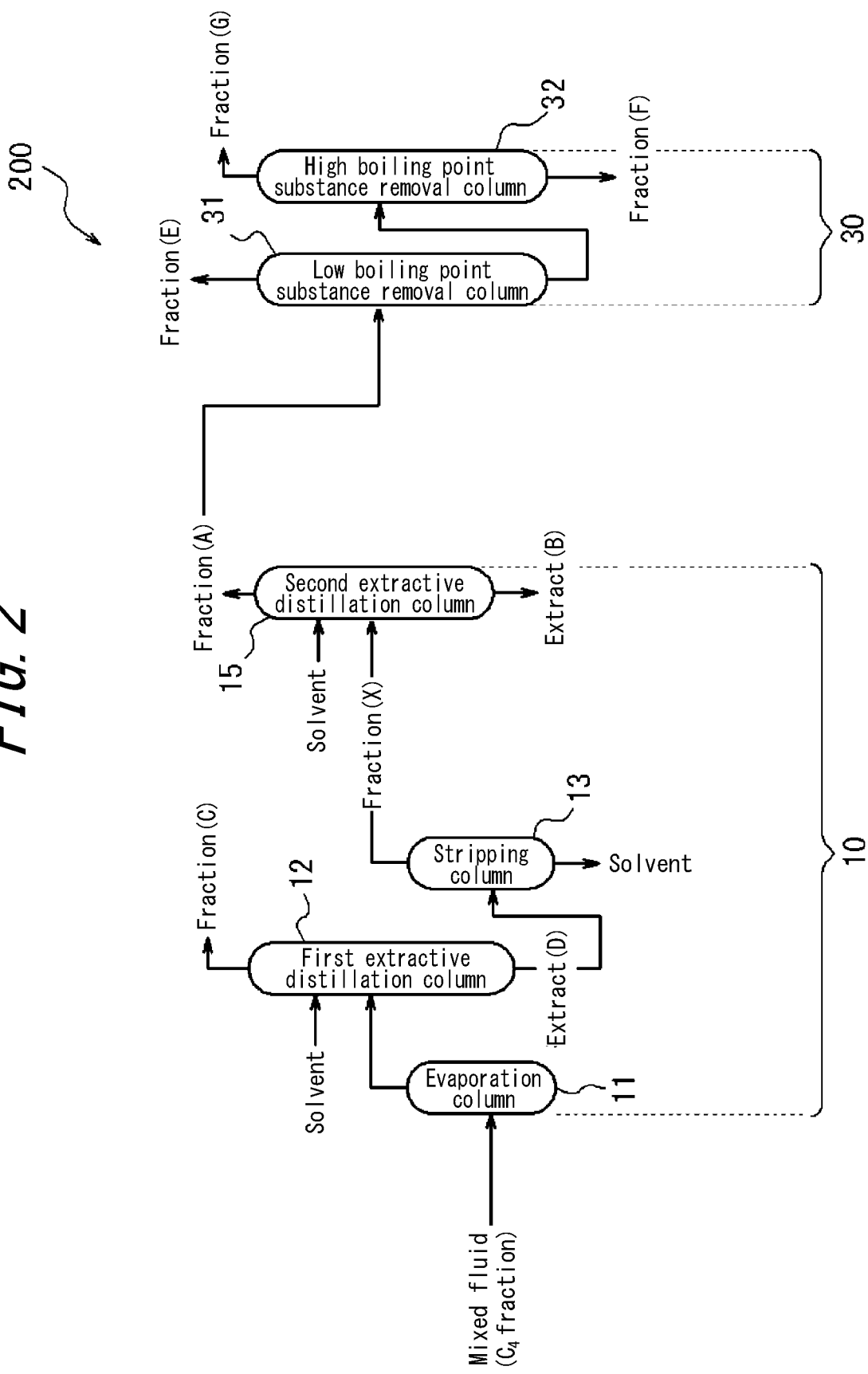
FIG. 2 schematically illustrates configuration of one example of a 1,3-butadiene separation and recovery apparatus for carrying out a conventional 1,3-butadiene separation and recovery method.

Separation and recovery of 1,3-butadiene was performed in the same manner as in Example 1 with the exception that a separation and recovery apparatus 200 illustrated in FIG. 2 was used instead of the separation and recovery apparatus 100 illustrated in FIG. 1 in Example 1.

Note that the separation and recovery apparatus 200 is the same with the exception that the dividing wall distillation section 20 in FIG. 1 was replaced with an impurity removal section 30.

<Impurity Removal Section>

The impurity removal section 30 includes a low boiling point substance removal column 31 that removes impurities having a lower boiling point than 1,3-butadiene that are contained in the fraction (A) obtained in the second extractive distillation column 15, and a high boiling point substance removal column 32 that removes impurities having a higher boiling point than 1,3-butadiene that are contained in the fraction (A) obtained in the second extractive distillation column 15.

In the low boiling point substance removal column 31, the fraction (E) containing impurities having a lower boiling point than 1,3-butadiene is distilled from the top of the column, and a bottom liquid in which 1,3-butadiene is enriched is drained from the bottom of the column.

In the high boiling point substance removal column 32, the fraction (G) in which 1,3-butadiene is further enriched is distilled from the top of the column, and the fraction (F) containing impurities having a higher boiling point than 1,3-butadiene is drained from the bottom of the column.

When operation was performed continuously for one year in Example 1 and Comparative Example 1 and then the inside of the distillation columns was visually inspected, the amount of the 1,3-butadiene polymer produced was small in Example 1 than in Comparative Example 1.

INDUSTRIAL APPLICABILITY

According to the 1,3-butadiene separation and recovery method and apparatus of the present disclosure, by performing dividing wall distillation, it is possible to reduce heat load and reduce the amount of the 1,3-butadiene polymer produced, and, it is also possible to reduce the frequency of polymer cleaning which needs to be performed with the operation of the 1,3-butadiene separation and recovery apparatus suspended.

REFERENCE SIGNS LIST

10 Extractive distillation section
11 Evaporation column
12 First extractive distillation column
13 Stripping column
15 Second extractive distillation column
20 Dividing wall distillation section
21 Dividing wall column
30 Impurity removal section
31 Low boiling point substance removal column
32 High boiling point substance removal column
100 Separation and recovery apparatus
200 Separation and recovery apparatus

The invention claimed is:

1. A 1,3-butadiene separation and recovery method for separating and recovering 1,3-butadiene from a mixed fluid containing 1,3-butadiene, comprising:
   an extractive distillation step of performing extractive distillation of the mixed fluid to obtain a fraction containing crude 1,3-butadiene; and
   a dividing wall distillation step of performing dividing wall distillation of the fraction containing crude 1,3-butadiene to obtain a fraction (F) containing an impurity having a higher boiling point than 1,3-butadiene, a fraction (E) containing an impurity having a lower boiling point than 1,3-butadiene, and a fraction (G) containing high-purity 1,3-butadiene by using a dividing wall column to distill the fraction (E) from the top of the column, drain the fraction (F) from the bottom of the column, and distill the fraction (G) from the region of the center of the column.

2. The 1,3-butadiene separation and recovery method according to claim 1, wherein an extractant used in the extractive distillation step is an amide compound.

3. The 1,3-butadiene separation and recovery method according to claim 2, wherein the amide compound is dimethylformamide.

4. The 1,3-butadiene separation and recovery method according to claim 1, wherein the dividing wall distillation in the dividing wall distillation step is performed in the presence of not less than 1 mass ppm and not more than 100 mass ppm of a polymerization inhibitor relative to the crude 1,3-butadiene.

5. The 1,3-butadiene separation and recovery method according to claim 1, wherein
   the dividing wall distillation in the dividing wall distillation step is performed in a dividing wall column, and
   a polymerization inhibitor is fed from a vertical direction upper part of the dividing wall column.

6. The 1,3-butadiene separation and recovery method according to claim 1, wherein the fraction containing high-purity 1,3-butadiene is a gas.

7. The 1,3-butadiene separation and recovery method according to claim 1, further comprising a step of removing a polymerization inhibitor from the fraction containing high-purity 1,3-butadiene.

8. A 1,3-butadiene separation and recovery apparatus comprising:
- an extractive distillation section that includes a feeding port for feeding of a mixed fluid containing 1,3-butadiene and that performs extractive distillation of the mixed fluid to obtain a fraction containing crude 1,3-butadiene; and
- a dividing wall distillation section that includes a dividing wall column that includes a feeding port for feeding of the fraction containing crude 1,3-butadiene and that performs dividing wall distillation of the fraction containing crude 1,3-butadiene to obtain a fraction (F) containing an impurity having a higher boiling point than 1,3-butadiene, a fraction (E) containing an impurity having a lower boiling point than 1,3-butadiene, and a fraction (G) containing high-purity 1,3-butadiene, wherein
- the dividing wall column distills the fraction (E) from the top of the column, drains the fraction (F) from the bottom of the column, and distills the fraction (G) from the region of the center of the column.

* * * * *